United States Patent [19]

Morishita et al.

[11] Patent Number: 4,873,087
[45] Date of Patent: * Oct. 10, 1989

[54] SUPPOSITORY PREPARATION HAVING EXCELLENT ABSORPTION PROPERTY

[75] Inventors: Masataka Morishita; Renji Aikawa; Shigeo Katsuragi; Yoshiaki Yamamoto; Kenichi Sugimoto, all of Shizuoka, Japan

[73] Assignee: Toyo Jozo Company, Ltd., Shizuoka, Japan

[*] Notice: The portion of the term of this patent subsequent to Sep. 10, 2002 has been disclaimed.

[21] Appl. No.: 355,887

[22] Filed: Mar. 8, 1982

[30] Foreign Application Priority Data

Jan. 14, 1982 [JP] Japan .................................. 57-4222

[51] Int. Cl.$^4$ .............................................. A61K 9/02
[52] U.S. Cl. .................... 424/433; 424/430; 424/436; 514/563; 514/613; 514/617; 514/946; 514/947; 514/966; 514/967; 514/2
[58] Field of Search ............... 514/563, 613, 617, 946, 514/947, 966, 967; 424/430, 433, 436

[56] References Cited

U.S. PATENT DOCUMENTS

| 3,091,569 | 5/1963 | Sheffner . |
| 3,782,971 | 1/1974 | Van Roon . |
| 3,825,664 | 7/1974 | Hagemann et al. . |
| 3,904,754 | 9/1975 | Morelle ............................ 514/563 |
| 4,609,640 | 9/1986 | Morishita et al. . |

FOREIGN PATENT DOCUMENTS

| 2470 | 4/1964 | France . |
| 1485602 | 6/1967 | France ................................. 424/61 |
| 2027476 | 9/1970 | France . |
| 2074632 | 10/1971 | France . |
| 1153408 | 5/1969 | United Kingdom . |
| 1322482 | 7/1973 | United Kingdom . |
| 1385914 | 3/1975 | United Kingdom . |
| 1468646 | 3/1977 | United Kingdom . |
| 1483500 | 8/1977 | United Kingdom . |
| 1485694 | 9/1977 | United Kingdom . |
| 2092002 | 8/1982 | United Kingdom . |

OTHER PUBLICATIONS

Sawai–Chem. Abst.–vol. 97 (1982) p. 44324r.
De Mill–Chem. Abst., vol. 92 (1980) p. 28585t.
Eberhardt et al–Chem. Abst., vol. 88 (1978), p. 197670q.

Primary Examiner—Sam Rosen
Attorney, Agent, or Firm—Antonelli, Terry & Wands

[57] ABSTRACT

A preparation containing an absorption promoter selected from N-acyl amino acid derivatives or N-acyl peptide derivatives represented by the formula: R-CO-A (R is an aliphatic hydrocarbon group, an aromatic hydrocarbon group or an aryl-substituted lower hydrocarbon group which may optionally be substituted, and A is an amino acid residue or a peptide residue), preferably in the presence of a salt at a concentration exhibiting higher osmotic pressure than isotonic sodium chloride solution, and a medicine is found to promote absorption of the medicine through a gastrointestinal organ such as the colon and rectum, and through the vagina.

9 Claims, 3 Drawing Sheets

SUPPOSITORY PREPARATION HAVING EXCELLENT ABSORPTION PROPERTY

This invention relates to a novel preparation having an excellent absorption property which is intended for improvement of absorption of a medicine poor in absorption property through the rectum or other digestive organs in a body by administration of such a medicine simultaneously with a water-soluble substance at a concentration exhibiting higher osmotic pressure than isotonic sodium chloride solution and one or more of an absorption promoter selected from N-acyl aminoacid derivatives or N-acyl peptide derivatives as represented by the formula: R—CO—A (1), (wherein R is an aliphatic hydrocarbon group, an aromatic hydrocarbon group, an aryl-substituted lower hydrocarbon group which may optionally be substituted and A is an amino acid residue or a peptide residue).

Absorption of a medicine through a digestive organ, irrespective of whether it may be stomach, small intestine, large intestine, rectum or mouth, has heretofore been generally believed to proceed according to pH Partition theory (Modern Pharmaceutics, Marcel Dekker, INC,. p. 31–49). Hence, a medicine readily dissociated in respective organs at absorption sites or a medicine having poor lipophilicity tends to be poorly absorbed. Such difficultly absorptive medicines are administered as injections under the present circumstances. For improvement of absorption property of a medicine, there have been made various investigations such as Prodrug, Sofdrug, utilization of ion pairs or complex formation. But any of these proposals is effective specifically for individual medicines, and no universally applicable method is known in the art ("Pharmaceutics" written by Nogami).

The present inventors have made various investigations and consequently found that in the mechanism of membrane absorption through digestive organs or others, which is believed to proceed according to the pH partitions theory as mentioned above, an N-acyl aminoacid derivative or an N-acyl peptide derivative which is represented comprehensively by the above formula (1) causes some changes in membrane permeability, whereby membrane absorption of a medicine can be improved to successfully promote absorption thereof. Further, it has also been found that membrane absorption can be markedly improved by addition of a water-soluble substance at a concentration exhibiting higher osmotic pressure than isotonic sodium chloride solution to make the preparation under a condition of higher tonicity than the osmotic pressure of a body fluid. In addition to these findings, it has further been found that a preparation obtained by use of a vehicle, additives selected as desired and an objective medicine, for example, a suppository to be inserted into the rectum or vagina, is a good suppository which can excellently be absorbed through membranes and maintain a high concentration of the medicine in blood for a long time. The medicines to be used in the present invention are very broad. In particular, so called water-soluble medicines having good solubility in water, for example, those with partition coefficients of 50 or less in chloroform/water or medicines readily dissociated into ions, are useful. Further, medicines applicable only as injections in the prior art are also found to be made excellently absorbable easily as preparations such as suppositories Even a medicine with a high molecular weight such as polypeptide is also found as the result of this invention to be made efficiently absorbable in the form of a preparation such as suppository.

The present invention has been accomplished based on the above findings, and the object of the present invention is to provide a good preparation in which a medicine can be improved to have a markedly enhanced absorption property.

In the accompanying drawings.

According to the present invention, a preparation is provided which comprises a water-soluble substance at a concentration exhibiting an osmotic pressure higher than isotonic sodium chloride solution, at least one absorption promoter selected from the group consisting of N-acyl amino acid derivatives or N-acyl peptide derivatives represented by the formula R—CO—A (1) (where R and A are the same as those defined above) and a medicine.

The water-soluble substance to be used in the present invention at a concentration exhibiting higher osmotic pressure than isotonic sodium chloride solution, may be preferably one which is harmless as a whole and can exhibit high osmotic pressure with as small an amount as possible.

As such a water-soluble substance, there may be included water-soluble salts and water-soluble sugars.

Particularly among water-soluble salts, sodium chloride is preferred since it is safe, its osmotic pressure is readily controlled, and it is soluble in water rapidly at a high dissolving rate. Further, mannitol or glucose is preferred among water-soluble sugars. Generally speaking, water-soluble salts may include, for example, halides, sulfates, phosphates or carbonates of alkali metals such as sodium, potassium or lithium, more specifically the aforesaid sodium chloride, sodium sulfate, disodium hydrogen phosphate, sodium dihydrogen phosphate, sodium phosphate, sodium hydrogen carbonate, sodium carbonate, potassium chloride, potassium sulfate, potassium hydrogen phosphate, potassium carbonate, lithium chloride, etc. These salts may be adjusted to concentrations exhibiting higher tonicity than osmotic pressure of isotonic sodium chloride solution depending on the osmotic characteristic thereof. For example, in case of sodium chloride, it may generally be adjusted to a concentration of 1 W/W % or higher of the whole content. The upper limit of the concentration is not particularly limited, but preferably the concentration is about 2 to 30 W/W %. As preferable water-soluble sugars, there may be employed monosaccharides or disaccharides frequently used for adjustment of osmotic pressure in pharmaceutical technology, including, for example, glucose, mannitol, sorbitol, xylitol, lactose, maltose and sucrose. Such a sugar may be used at a concentration with higher tonicity than isotonic sodium chloride solution, which is generally 0.25M or higher. These water-soluble substances may be used in combination of two or more kinds for adjustment of osmotic pressure, which is preferably 1.5 to 6-fold of the osmotic pressure exhibited by isotonic sodium chloride solution.

In connection with osmotic pressure, description is herein made by comparison with isotonic sodium chloride solution, but such description with the use of isotonic sodium chloride solution as Control is merely exemplary for comparison between osmotic pressure, and therefore it may also be possible to use of body fluids or other solutions of salts with tonicity equal to such isotonic sodium chloride solution.

Referring now to the N-acyl aminoacid derivatives or N-acyl peptide derivatives which are represented by the formula R—CO—A (1) (R and A are same as those defined above) to be used as an absorption promoter in this invention, they were investigated by adding them to, for example, an isotonic preparation for rectal application containing a medicine for examination of the increase or decrease of membrane permeability of the medicine to accomplish the present invention. The mechanism of the promotion effect has not so far been clarified, but it seems likely that the membrane absorption mechanism may be changed through the chelating action and affinity to membrane possessed by these absorption promoters on the structures of cell membranes or the spaces between the epitherial cells thereby promoting absorption.

Although the mechanism action of the absorption promoter for increasing drug absorption through the rectum or other organs may be speculated as mentioned above, such a mechanism action is still no more than mere estimation and it is only sufficient to employ N-acyl aminoacid derivatives or N-acyl peptide derivatives having chelating action capable of bonding to at least calcium ions or magnesium ions.

Further, referring to the N-acyl amino acid derivatives or N-acyl peptide derivatives of the formula (1), these compounds are obtained in this invention by reacting an acid compound of the formula:

R—COOH             (2)

(wherein R is the same as that defined above) or its reactive derivative of carboxyl group with a compound of formula (3):

H—A             (3)

(wherein H—A is an amino acid or a peptide) or its derivative having protected carboxyl group. Alternatively, the compound of the formula (1) may also be obtained by condensation of an acyl group of the above acid compound (2) and the amino residue group or the imino residue group of an amino acid or a peptide.

Carboxyl groups can be activated by agents such as an acid azide, an acid anhydride, an acid imidazolide, an acid halogenide, an active ester or a carbodiimide, an N,N'-carbonyldiimidazole or an isoxazolium salt such as Woodward's reagent.

The preferred condensation reaction in the present invention is the carbodiimide, azide, active ester, halogenide or anhydride method.

As example of condensed reaction, amino acid or peptide is reacted with reactive derivatives of acid-compound of formula (2) in an inert medium, for example, an organic solvent such as chloroform, methylenechloride, ethylenechloride, ether and hydrophilic solvent or an aqueous hydrophilic solvent such as water, methanol, ethanol, acetone, dimethylacetoamide, dimethylformamide and dioxane. N-acylation is performed by a usual method, and if necessary, a condensation agent or a base may be added to the above solvent.

In this reaction, the reaction temperature is below or at room temperature, and the acid compound of formula (2) is used about one mole per mole of amino acid or peptide. After the reaction, it may be purified by preferably, a method of gel filtration.

As an acid-compound of the formula (2), there may preferably be used an acid in which R is an aliphatic hydrocarbon group which may be substituted or an aromatic hydrocarbon group which may be substituted or an aryl-substituted lower aliphatic acid in which the number of carbon atoms of the lower aliphatic acid group is generally in the range of 1 to 10, preferably 1 to 5, which may be substituted.

When R is an aliphatic hydrocarbon group which may be substituted, the hydrocarbon group may have generally in the range of from 1 to 20 carbon atoms, preferably 4 to 18. As aliphatic acids having such groups, there may be mentioned, for example, acetic acid, propionic acid, butyric acid, valeric acid, isovaleric acid, hexanoic acid, enathic acid, octanoic acid, pelargonic acid, decanoic acid, undecylic acid, lauric acid, myristic acid, palmitic acid, stearic acid, acrylic acid, crotonic acid, vinylacetic acid, 4-pentenoic acid, oleic acid, linoleic acid, linolenic acid or sorbic acid as fatty acid and these compounds substituted with a lower alkyl group, hydroxyl group, carboxylic acid group, alkoxy group, phosphoric acid group, amino group, imino group or a halogen.

As acids wherein R is an aromatic hydrocarbon group which may be substituted, there may be mentioned, for example, benzoic acid, alkylbenzoic acid, phthalic acid, isophthalic acid, o-, m- or p-aminobenzoic acid, o-, m- or p-hydroxybenzoic acid, o-, m- or p-alkoxybenzoic acid, dihydroxybenzoic acid and these compounds substituted with above functional groups.

Acids wherein R is an aryl-lower-hydrocarbon group which may be substituted may include, for example, phenylacetic acid, phenylpropionic acid, o-, m- or p-hydroxy phenylacetic acid, phenylmalonic acid, phenylsuccinic acid, cinnamic acid, phenylpyruvic acid, benzoylacetic acid and these compounds substituted with above functional groups.

As an amino acid or a peptide of the formula (3), natural amino acid or peptide may preferably be used. They can be in either D-, L- or DL-form, and the derivatives thereof substituted with hydroxyl, amino, carboxylic acid, lower hydrocarbon, alkoxy, phosphoric acid or a halogen atom as well as ethyl or methyl ester derivatives thereof are also available. There may be mentioned, for example, various natural amino acids (Chemistry of Amino Acids, Vol. 1, p. 3–8 etc ) o-, m- or p-hydroxy phenylalanine, o-, m- or p-hydroxy phenylglycine, $\alpha$-, $\beta$- or $\gamma$-carboxy glutamic acid, glutamic acid $\alpha$-methylester, glutamic acid $\alpha$-ethylester, aspartic acid $\alpha$-ethylester, $\alpha$-, $\beta$- or $\gamma$-amino butyric acid, iminodiacetic acid and others.

As the peptide to be acylated, there may generally be used a peptide composed of two or more amino acids, preferably of 2–4 amino acids by conventional synthetic methods. These N-acyl amino acid derivatives or N-acyl peptide derivatives preferably possess a chelating activity of about one-thousandth or more of EDTA (ethylenediaminetetraacetic acid).

These N-acyl amino acid derivatives or N-acyl peptide derivatives mentioned above are preferably used in the form of alkali metal salts such as sodium salts, potassium salts or ammonium salts.

An N-acyl amino acid derivative or an N-acyl peptide derivative which is represented by the above formula (1) is used in the present invention as an absorption promoter.

These absorption promoters may be employed in amounts of 0.01 W/W % or more, generally in the range of from 0.1 to 30 W/W %, preferably from 1.0 to 20 W/W %. As the vehicle to be employed for preparation of a suppository containing the above absorption promoter, a medicine and preferably a water-soluble salt to be added for increasing tonicity, there may suitably be selected one from oily vehicles and water-soluble vehicles conventionally used in preparation of suppositories or rectal injections, and a surfactant may also be added if desired.

As these oily vehicles or water-soluble vehicles, there may conveniently be used those as described in "The Theory and Practice of Industrial Pharmacy", p. 245 to 269 (1976).

The medicine to be used in the present invention is not particularly limited, but there may be employed ordinary pharmaceuticals, particularly preferably so called water-soluble medicines which are excellently soluble in water, such as water-soluble medicines with a partition coefficient of 50 or less in chloroform/water or medicines readily dissociated to ions. For example, there may be included various medicines such as hypnotics, tranquilizers, antiepileptics, antipyretics, antalgics, antidepressants, muscle relaxants, antiinflammatory agents, antiallergic agents, immunosuppressants, antirheumatics, vasodilators, antihemorragics, antihypertensives, antibiotics, antibacterial agents, urinary tract sterilizers, antitumor agents, vitamins, hormones and galenicals. More specifically, typical examples are penicillin type antibiotics such as ampicillin, hetacillin, amoxicillin, cyclacillin, cloxacillin, dicloxacillin, oxacillin, carindacillin, sulbenicillin, piperacillin, apalcillin, methycillin, etc. or combined drugs of ampicillin or amoxicillin with oxacillin, cloxacillin, floxacillin or dicloxacillin; cephalosporin type antibiotics such as cephalothin, cephazolin, cephaloridine, cephacetorile, cefoxitin, cefadroxil, cefatridine, cephaloglycin, cephalexin, cephapirin, cephachlor, ceftexol, cefuroxime, cefsulodin, cefmetazole, etc. and non-toxic salts thereof such as alkali metal salts (e.g. sodium salts or potassium salts), ammonium salts or benzylamine salts. In addition, there may also be mentioned tetracycline type antibiotics such as doxycycline, oxycycline, etc; aminosaccharide type antibiotics such as kanamycin sisomicin, amikacin, tobramycin, netromycin, gentamycin, 1-N-(s-3-amino-2-hydroxypropionyl)-gentamicin B, etc.; peptide type antibiotics such as tuberactinomycin N, actinomycin, etc. or non-toxic salts thereof; further peptide hormones such as insulin, somatostatin, calcitonin, angiotensin, kallikrein, secretin, gastrisin, parathyroid hormone, etc.; and other medicines such as barbital, theophylline, aspirin, mizoribin (bredinine), 5-fluorouracil, methotrexate, L-dopa, etc. The medicine may be employed in an amount, which may be suitably selected and designed. For example, in case of antibiotics such as β-lactam antibiotics, 20 to 500 mg activity, generally 100 to 300 mg activity, or in case of peptide hormones such as insulin, 1 to 500 units may be contained per gram of preparation. In general, the medicine may preferably be used in finely divided forms with 1 to 50μ diameters or as an aqueous solution.

The step of forming preparations may be performed according to conventional methods for production of preparations in general such as rectal suppository, urethral suppository or vaginal suppository, ointments or creams. For example, the absorption promoter selected, a water-soluble substance in an amount exhibiting higher osmotic pressure than isotonic sodium chloride solution and a medicine are added to a vehicles, optionally in combination with a surfactant, and these components are thoroughly mixed to provide preparations.

Further, in production of these preparation, there may also be added preservatives such as methyl- or propyl-p-oxybenzoate, colorants, aromas and stabilizers.

The present invention is further illustrated in detail by referring to the following Examples, by which the present invention is not limited at all but various medicines, hypertonicators and absorption promoters may be selected and combined in addition to those shown in Examples.

The abbreviations of employed in Examples are as follows,
Gly: Glycine
Pro: Proline
Phe: Phenylalanine
Asp: Aspartic acid
Glu: Glutamic acid
Val: Valine
Thr: Threonine
Ile: Isoleucine
Phy Phenylglycine
Lys: Lysine
$\epsilon$-Acp: $\epsilon$-Aminocaproic acid
OEt: Ethyl ester
OMe: Methyl ester
Boc: t-Butyloxy carbonyl
HOBt: 1-Hydroxy benzotriazole
TFA: Trifluoroacetic acid
DMF: Dimethyl formamide
WSCD: N-Ethyl, N-3-dimethylaminopropyl carbodiimide
AcOEt: Ethyl acetate
NMM: N-Methyl morpholine
EtOH: Ethanol
HCl: Hydrochloric acid
NaOH: Sodium hydroxide
TMA: Trimethyl amine

EXAMPLE 1

Absorption effects under conditions with various tonicities were examined. Each sample solution was prepared by adding 0.1 W/V % cephalothin Na as a medicine together with 0.01 W/V % N-lauroyl Gly-ONa as an absorption promoter to a phosphate buffer of pH 7.5 conditioned with sodium chloride to a tonicity which was varied from isotonic to twice hypertonic than isotonic (two-fold tonicity), four times hypertonic than isotonic (four-fold tonicity).

The experiment was conducted according to the following method. Namely, Wistar-strain male rats, weighing 250 to 300 g, were narcotized (after fast for 20 hours) with pentobarbital (50 mg/kg) and thereafter subjected to hypoabdominal incision for a first cannulation at a position about 1.5 cm from anus and also another cannulation at a position 5 cm upper than said first cannulation. Subsequently, the rectum was internally washed with about 20 ml isotonic sodium chloride solution kept at 38° C., and samples each of 10 ml were circulated through the rectum for 5 minutes (2 ml/minute) to make the concentration in the system constant. Then, 5 ml of each sample was circulated at a flow rate of 2 ml/minute, and samples each of 0.05 ml were collected at intervals of 10 minutes from 0 minute. Each sample was diluted to 5 ml with distilled water and the quantity of medicine disappeared by absorption was determined by UV-spectro photometer.

Figure 1:
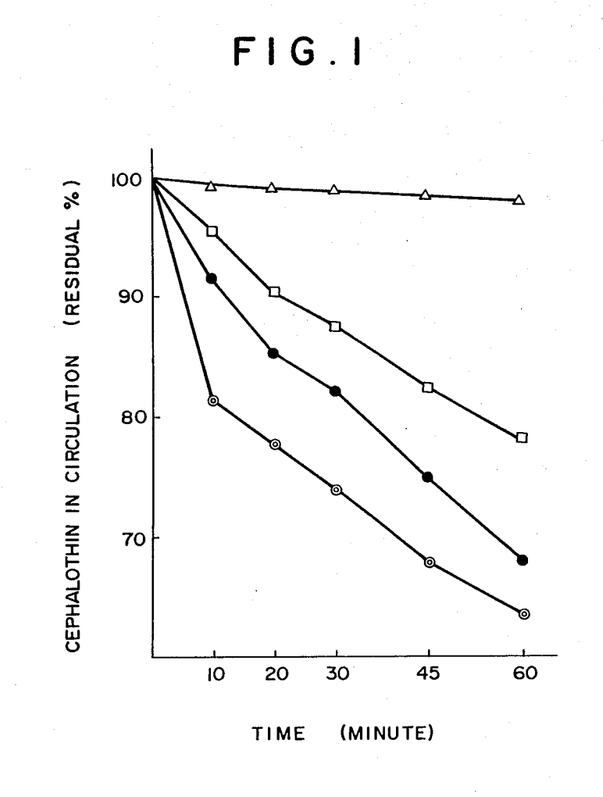
FIGS. 1 and 2 show disappearance curves for various osmotic pressures of Cephalothin Na when using Cephalothin Na as medicine, in which the percentages of Cephalothin disappeared by absorption are plotted at various measurement time.

As the result, the disappearance curve of Cephalothin-Na under the condition of 0.01 W/V % N-lauroyl Gly-ONa was obtained as shown in FIG. 1, in which □–□shows the result under the isotonic condition, ●–● under two-fold tonicity, ⊚–⊚ under four-fold tonicity and △–△ under no absorption promoter (Control)

EXAMPLE 2

Figure 2:
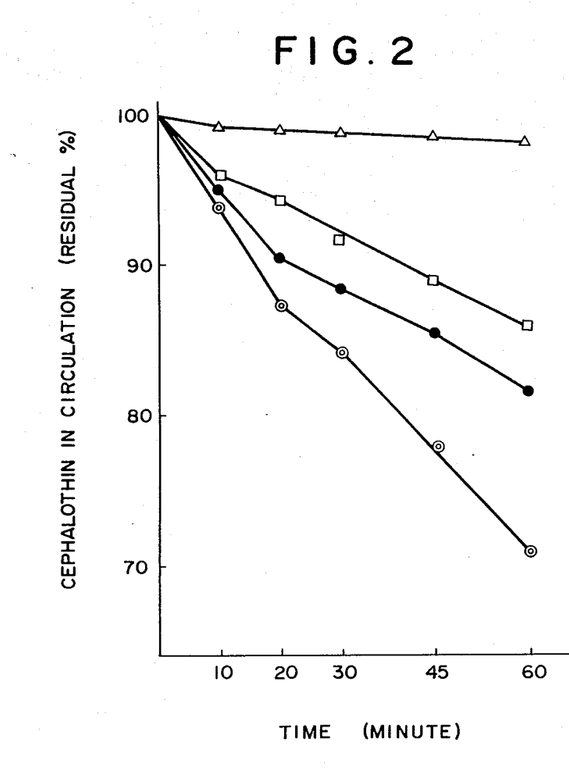

Using 0.1 W/V % cephalothin Na as a medicine and 0.1 W/V % of N-myristoyl Pro-Pro-GlyNa as an absorption promoter under respective osmotic pressure conditions (namely isotonic, two fold tonicity and four fold tonicity with the use of sodium chloride) and following otherwise the same procedure as in Example 1, quantities of Cephalothin disappeared by absorption were determined. The results are shown in FIG. 2, in which □–□ shows the result under the isotonic condition, ●–● under two-fold tonicity, ⊚–⊚ under four-tonicity and △–△Control.

EXAMPLE 3

Quantities of 0.1 W/V % Cephalothin Na disappeared by absorption under isotonic and two-fold tonic and four-fold tonic conditions were determined, respectively, using N-acyl amino acids and N-acyl peptides where the N-acyl groups are aliphatic hydrocarbons, similarly as in Example 1. The results are shown in Table 1.

TABLE 1

| (values after 60 mintues) | | | |
|---|---|---|---|
| | Isotonic condition | Two-fold tonic condition | Four-fold tonic condition |
| N—Propionoyl PheONa | 7.3% | —% | 19.2% |
| N—Hexanoyl PheONa | 13.5 | 20.9 | 37.6 |
| N—Octanoyl PheONa | 22.5 | 31.7 | 42.1 |
| N—Octanoyl PheOH | 12.5 | — | 25.5 |
| N—Hexanoyl ValONa | 4.7 | — | 16.2 |
| N—Hexanoyl GlyONa | 18.6 | 25.8 | 34.8 |
| N—Octanoyl GlyONa | 20.5 | 26.4 | 34.7 |
| N—Decanoyl GlyONa | 19.5 | 24.6 | 36.2 |
| N—Myristoyl GlyONa | 10.1 | — | 20.4 |
| N—Hexanoyl AspONa | 21.0 | — | 34.0 |
| N—Octanoyl AspONa | 19.5 | — | 31.0 |
| N—Decanoyl AspONa | 16.9 | — | 26.4 |
| N—Lauroyl AspONa | 21.8 | 35.8 | 47.4 |
| N—Myristoyl GlyONa | 10.3 | 15.7 | 20.7 |
| N—Decanoyl Pro-Pro-GlyONa | 7.8 | 14.0 | 20.3 |
| N—Lauroyl Pro-Pro-GlyONa | 12.4 | — | 22.4 |
| N—Myristoyl Pro-GlyONa | 9.5 | 15.4 | 20.6 |
| No adjuvant | 2.1 | 3.3 | 6.2 |

EXAMPLE 4

Quantities of 0.1 W/V % Cephalothin.Na disappeared by absorption under isotonic, two-fold tonic and four-fold tonic conditions were determined by the high pressure liquid chromatography respectively, using N-acyl amino acids and N-acyl peptide in which the N-acyl groups are aromatic hydrocarbons and aryl-substituted low hydrocarbons, similarly as in Example 1. The results are shown in Table 2.

TABLE 2

| (values after 60 mintues) | | | |
|---|---|---|---|
| | Isotonic condition | Two-fold tonic condition | Four-fold tonic condition |
| N—Benzoyl AlaONa | 22.6% | 30.1% | 39.8% |
| N—Benzoyl ThrONa | 23.5 | 28.7 | 40.0 |
| N—Benzoyl ε-AcpONa | 20.7 | 32.3 | 37.7 |
| N—Phenacetyl LysONa | 7.6 | — | 17.8 |
| N—Phenacetyl IleONa | 11.8 | — | 21.9 |
| p-Aminobenzoyl GlyONa | — | 16.2 | 22.5 |
| N—Phthaloyl GluONa | 24.1 | 27.3 | 30.4 |
| N—Phthaloyl Glu α-methyl ester | 22.7 | — | 32.4 |
| N—Phthaloyl IleONa | 23.1 | 30.4 | 35.1 |
| N—Benzoyl GlyAspONa | 12.7 | — | 25.1 |

EXAMPLE 5

Figure 3:
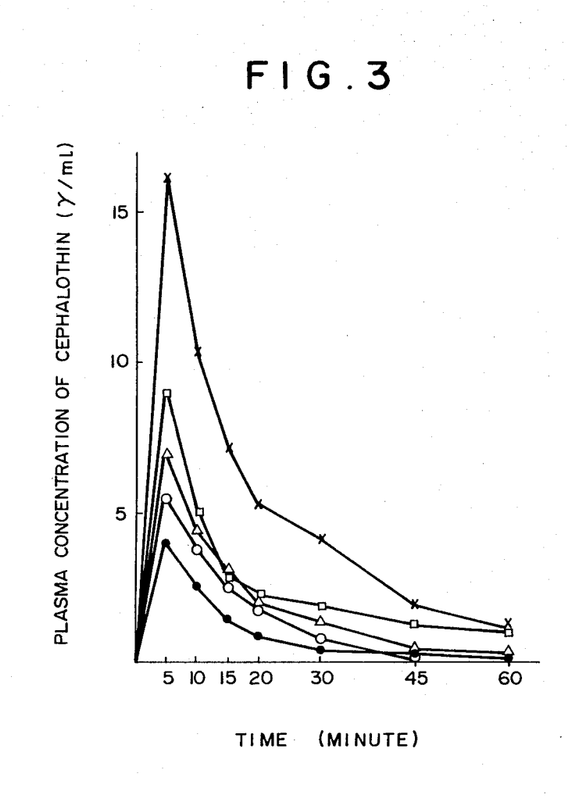
FIG. 3 shows a curve of plasma concentration of Cephalothin when using Cephalothin Na as medicine.

Cephalothin.Na (600 mg potency) as a medicine, N-acyl peptides (100 mg) as an absorption promoter and sodium chloride (200 mg) as a hypertonicator were each pulverized and dispersed in 1 ml of distilled water. A homogeneous dispersion was prepared by adding the resulting mixture to a base of Witepsol H-15 previously molten by fusion to a total amount of 10 g. The dispersion was intrarectally administered at a dose of 30 mg/kg to Wister strain rats (male, weighing 200–250 g, four per one group) and blood sampling was performed 5 minutes, 10 minutes, 15 minutes, 20 minutes, 30 minutes, 45 minutes and 60 minutes after administration for measurement of Cephalothin concentration in plasma (according to the bioassay using Bacillus subtilis ATCC 6633). As Controls, there was also obtained a preparation without use of the absorption promoter (Control 1). N-Acyl peptides as the absorption promoter used were N-Myristoil Pro-Pro-GlyONa, N-Lauroyl Pro-Pro-GlyONa, N-Decanoyl Pro-Pro-GlyONa and N-Myristoyl Pro-GlyONa. The result are shown in FIG. 3, wherein ●–● indicates plasma concentration curve of Cephalothin in the case of control, □–□ that in case of N-Myristoyl Pro-Pro-GlyONa as the absorption promoter, ○–○ that in case of N-Lauroyl Pro-Pro-GlyONa, △–△that in case of N-Decanoyl Pro-Pro-GlyONa and x—x that in case of N-Myristoyl-Pro-GlyONa, respectively.

EXAMPLE 6

Figure 4:
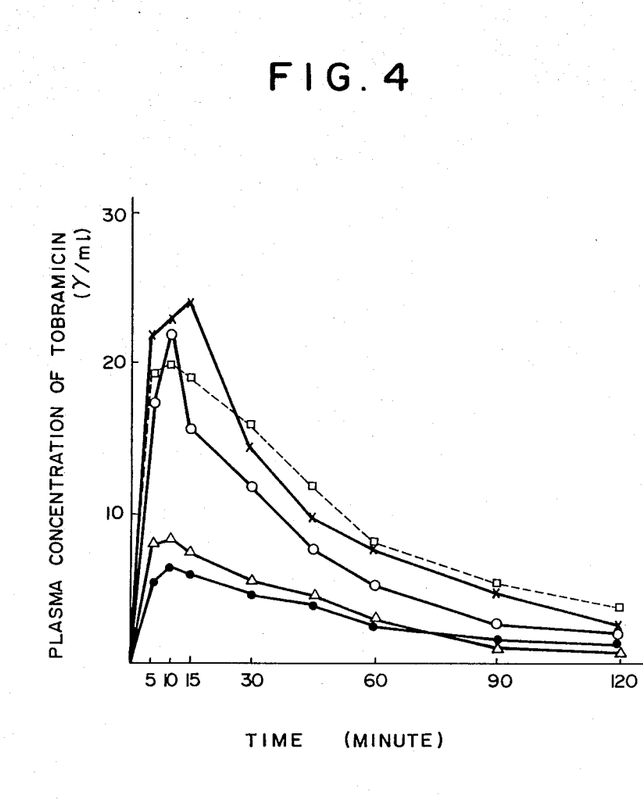
FIG. 4 shows a curve of plasma concentration of Tobramicin when using Tobramicin as medicine.

Tobramycin (200 mg potency) as a medicine, N-acyl amino acids (10 mg) as a absorption promoter and sodium chloride (200 mg) as a hypertonicator were each pulverized and mixed together. The mixture was mixed with Witepsol H-15 molten by heating to an amount of 1 g. The dispersion was intrarectally administered at a dose of 20 mg$^p$/kg and experiment was carried out similarly as in Example 5. As Control, there was also obtained a preparation without use of the absorption promoter N-acyl aminoacids as the absorption promoters used were N-Lauroyl PheONa, N-Butyryl PheONa, N-Lauroyl PhyONa and N-Butyryl PhyNa. The results are shown in FIG. 4, wherein ●–● indicates plasma concentration curve of Tobramycin in the case of Control, △–△that in case of N-Butyryl PheONa, ○–○ that in case of N-Butyryl PhyONa, □–□ that in case of N-Lauroyl PheONa and x—x N-Lauroyl PhyONa, respectively.

EXAMPLE 7

Figure 5:
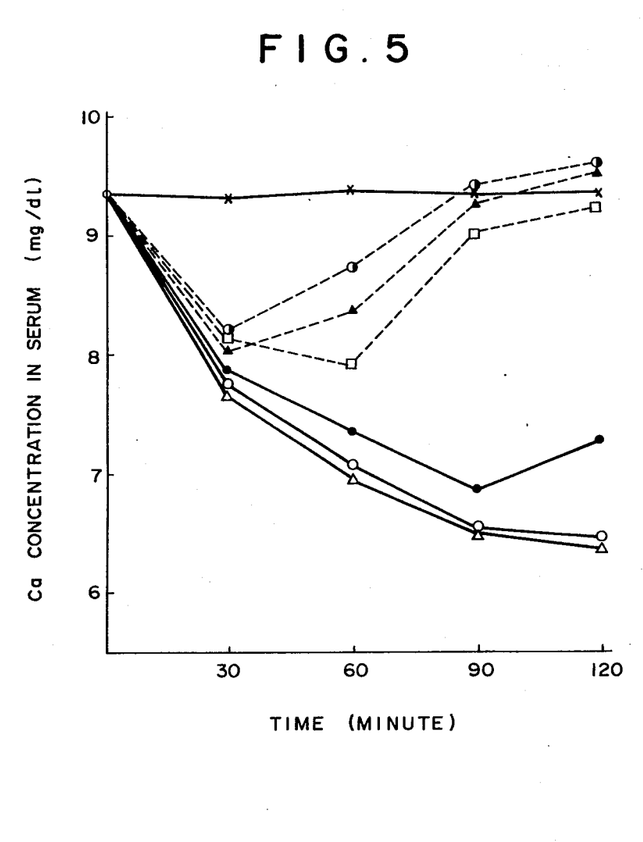
FIG. 5 shows a curve of calcium concentration in serum when using Elcitonin as medicine.

Elcitonin (Asu$^{1.7}$-eel calcitonin) (10 units and 2 units), N-acyl amino acids, N-acyl peptide and sodium chloride (50 mg) were dissolved in 1 ml of 5 % gelatin solution. Each solution (0.1 ml) was administered intrarectally to SD-strain male rats (four weeks of age) and calcium concentrations in serum were measured at 30 minutes, 60 minutes, 90 minutes and 120 minutes after administration by atomic absorption method. As Control, there was used a solution containing no absorption promoter (adjusted to 10 units of Elcitonin). N-acyl amino acids and N-acyl peptide as the absorption promoter used were N-Lauroyl GlyONa, N-Hexanoyl PheOH, N-Myristoyl Pro-Pro-GlyONa and N-Lauroyl AspONa. The results are shown in FIG. 5, wherein x—x indicates calcium concentration in serum in case of Control, ▲-▲ that in case of solution containing 2 units of Elcitonin and N-hexanoyl PheONa, ○-○ that in case of 2 units of Elcitonin and N-Lauroyl AspONa, □-□ that in case of 2 units of Elcitonin and N-Lauroyl GlyONa, ●-● that in case of 10 units of Elcitonin and N-Myristoyl Pro-Pro-GlyONa, ○-○ that in case of 10 units of Elcitonin and N-Hexanoyl PheOH and △-△ that in case of 10 units of Elcitonin with N-Lauroyl GlyONa.

EXAMPLE 8

Figure 6:
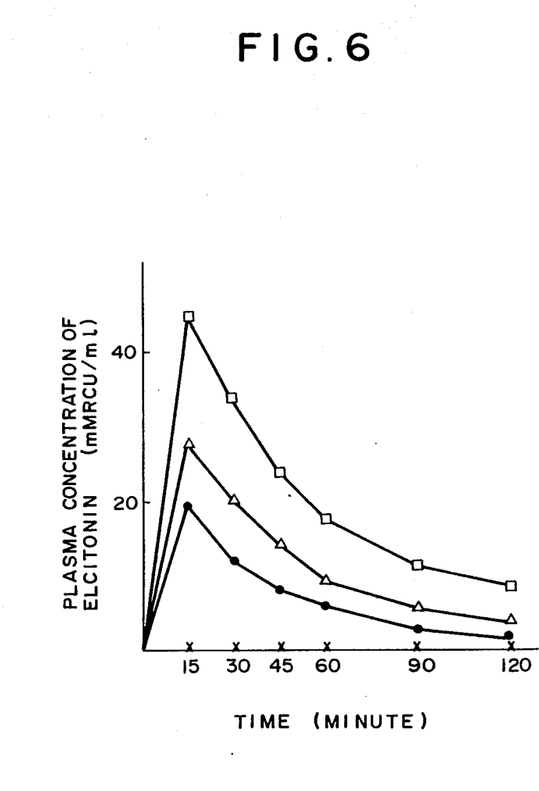
FIG. 6 shows a curve of plasma concentration of Elcitonin when using Elcitonin as medicine.

Elcitonin (Asu$^{1.7}$-eel calcitonin) of 200 units, N-acyl amino acids as the absorption promoter (50 mg) and sodium chloride (50 mg) were dissolved in 1 ml of a 5% gelatin solution. Each solution (0.1 ml) was administered intrarectally to Wister-strain rats (200–250 g) and Elcitonin concentration in plasma were determined by enzyme-immunoassay method at 15, 30, 45, 60, 90 and 120 minutes after administration. N-acyl amino acids as the absorption promoter used were N-Octanoyl GlyONa, N-Octanoyl PheONa and N-Lauroyl GlyONa. As Control, there was used a solution containing no absorption promoter. The results are shown in FIG. 6, wherein □-□ indicates Elcitonin concentration in plasma in case of N-Lauroyl GlyONa, △-△ that in case of N-Octanoyl GlyONa, ●-● that in case of N-Octanoyl PheONa and x—x that in case of Control. Further, Elcitonin concentration was not detectable in case of Control.

EXAMPLE 9

Cephalothin.Na (200 g potency), N-lauroyl GlyONa (50 g) and sodium chloride (50 g), each being pulverized, were mixed and the resulting mixture was dissolved in 2 % gelatin solution to a volume of one liter, which was then filled into injection cylinders in aliquots each of 1 ml to provide intrarectal injection preparations.

EXAMPLE 10

Gentamycin (100 g potency), N-Decanoyl AspONa (50 g) and mannitol (250 g), each being pulverized, were mixed and the mixture was homogeneously dispersed in 5 % gelatin solution to a volume of one liter, which was then filled into injection cylinders in aliquots each of 1 ml to provide intrarectal injection preparations.

EXAMPLE 11

One thousand units of Elcitonin, 50 g of N-Hexanoyl PheONa and 250 g of mannitol were each pulverized and mixed together. The resulting mixture was dispersed homogeneously in 5 % gelatin solution to a volume of one liter, which was then filled into injection cylinders in aliquots each of 1 ml to provide injection preparations for vaginal suppository.

EXAMPLE 12

One thousand units of Elcitonin, 50 g of N-Myristoyl Pro-GlyONa and 5 g of sodium chloride were dissolved in 100 ml of distilled water and the solution was added to Witepsol H-5 containing 1 % Span 60 (produced by Kao-Atlas Co.) to an amount of 500 g, followed further by homogeneous emulsifying. The emulsion was filled in suppository containers in aliquots each of 1 g to provide rectal suppositories.

EXAMPLE 13

Cefoxitin.Na (200 g potency), N-phthaloyl GlyONa (50 g) and sodium chloride (50 g) each being pulverized were mixed and dispersed in Witepsol H-5 molten by heating to an amount of 1 kg, which was then filled in suppository containers in aliquots each of 1 g to provide suppositories.

EXAMPLE 14

Example 13 was repeated except that Cefazolin.Na (200 g potency) was employed in place of Cefoxitin.Na to obtain suppositories.

EXAMPLE 15

1-N-(s-3-amino-2-hydroxypropionyl) gentamycin B (100 g potency), N-Hexanoyl GlyONa (10 g) and sodium chloride (50 g) were each pulverized and mixed. The mixture was mixed and homogeneously dispersed with Witepsol H-5 molten by heating to an amount of 1 kg. The dispersion was molded in suppository containers to provide suppositories each of 1 g.

EXAMPLE 16

GlyOEt.HCl (29.31 g), Boc-Pro (43.05 g), HOBt (28.37 g) in DMF (150 ml) was treated with WSCD (38.43 ml) in an ice-bath, and stirred for 2 hrs. at 0° C., further overnight at room temperature. The reaction mixture was evaporated in vacuo. The residue was dissolved in 1 l of AcOEt and washed with 5 % aqueous sodium bicarbonate solution, aqueous NaCl solution, 1-N HCl, 1-N NaOH and distilled water in this order. The solvent was evaporated in vacuo after dehydration to give a slightly yellowish oily product. (Boc-Pro-GlyOEt; 70.2 g).

The oily product in methylene chloride (20 ml) was treated with 70 ml of TFA at 0° C. and stirred for 30 minutes at room temperature. The solvent was evaporated and resulting oily residue was added to NMM for neutralization at 0° C. Myristic acid (7.54 g) in THF (50 ml) was treated with WSCD (6.59 ml) at 0° C., then stirred for 1 hr. and added to above neutralized solution and stirred overnight at room temperature. This reaction mixture was concentrated and dissolved in chloroform (300 ml) and washed with 5 % sodium bicarbonate, 1N-HCl, 1N-NaOH and distilled water in this order. The solution was concentrated after dehydration with sodium sulfate and applied to Sephadex L-20 column (4×120 cm), and eluted with Benzene-AcOEt (1:1). The fraction was applied to TLC on silica gel by the following solvent system (CHCl$_3$:MeOH:AcOH 95:5:3), the part of Rf=0.30 was collected and extracted with CHCl$_3$. This solution was evaporated in vacuo and an oily product was obtained (N-myristoyl Pro-GlyOEt). Yield 76.8%.

The product was dissolved in EtOH (30 ml) and 1N-NaOH (33 ml) was added to the solution at 0° C. The resultant solution was stirred for 1 hrs. at room temperature and evaporated in vacuo. The concentrated solution was applied to a column of Sephadex L-20 (4×120 cm). The UV absorption at 230 nm was determined in each fraction (12.5 ml each). The fraction corresponding to the main peak (tube No. 95-111) were combined and freeze dried after concentration. White powders are obtained (N-Myristoyl Pro-GlyONa). Yield 56.6%, m.p. 145°-148° C. Rf=0.80 (n-Butanol:Acetic acid:H$_2$O 3:1:1). Amino acid ratio in a 6-N-HCl hydrolysate: Proline 0.90, Glycine 1.00 Calcd. for: C, 59.70; H, 9.31; N, 6.92. Found: C, 59.61; H, 9.2; N, 7.22.

EXAMPLE 17

Using GlyOMe·HCl (30.2 g), Boc-Proline (4.3 g), HOBt (28.37 g) and WSCD (38.43 ml), the process was carried out similarly as in Example 16, whereby slightly yellowish oily product was obtained (BOc-Pro-GlyOMe). The product (10.31 g) in dioxane (5ml) was added to 4.32 N-HCl in dioxane (30 ml) in an ice bath, then stirred for 30 min. at room temperature. The solution was evaporated and dried in vacuo, thereafter dissolved in DMF (30 ml) and neutralized by addition of NMM (0.5 ml). Boc-Proline (6.46 g), HOBt (4.05 g) in DMF (30 ml) was treated with WSCD (5.49 ml) and stirred for 30 min. in an ice bath. The solution was added to above neutralized solution and stirred for 2 hrs. at 0° C. and further overnight at room temperature. The solution was evaporated and dissolved in CHCl$_3$ (300 ml), then washed with 5 % aqueous sodium bicarbonate solution, 1N-HCl, 1N-NaOH in this order. The solution was dehydrated and concentrated to give an oily product (16.84 g) (Boc-Pro-Pro-GlyOMe). Rf=0.65 (CHCl$_3$:EtOH:AcOEt 5:2:5).

The product was acylated to N-Myristoyl Pro-Pro-GlyOMe (8.50 g) in the same manner as in Example 16. The oily substance dissolved in EtOH (30 ml) was added to 1N-NaOH solution (20.08 ml) and stirred for 30 min., then applied to Sephadex L-20 column. The main fraction was collected, concentrated and freeze dried to obtain white powders (4.61 g) (N-Myristoyl Pro-Pro-GlyONa).

Yield: 54.9%, Rf=0.66 (n-BuOH:AcOH:H$_2$O 3:1:1). Calcd. for: C, 60.10; H, 8.92; N, 8.09. Found: C, 59.89; H, 9.20; N, 7.82. Amino acid ratio in a 6N-HCl hydrolysate: Proline 1.90, Glycine 1.00.

EXAMPLE 18

The process was carried out similarly as in Example 17, using capric acid instead of myristic acid, then N-Decanoyl Pro-Pro-GlyONa (7.22 g) was obtained. Yield: 81.0%, Rf=0.66 (n-BuOH:AcOH:H$_2$O 3:1:1)

Amino acid ratio in a 6N-HCl hydrolysate: Proline 1.8, Glycine 1.0. Calcd. for: C, 54.87; H, 8.38; N, 8.73. Found: C, 55.03, H. 8.62; N, 8.39.

EXAMPLE 19

The process was carried out similarly as in Example 17, using lauric acid instead of myristic acid, whereby N-lauroyl Pro-Pro-GlyONa (5.29 g) was obtained. Yield: 73.4 %, Rf=0.66 5 (n-BuOH:AcOH:H$_2$O 20 3:1:1).

Amino acid ratio in a 6N-HCl hydrolysate: Proline 1.9, Glycine 1.0 Calcd. for: C, 58.64; H, 8.61; N, 8.55. Found: C, 59.01; H, 8.90; N, 8.20

We claim:

1. A suppository having excellent absorption property, comprising (1) a water-soluble medicine, (2) a water-soluble substance selected from the group consisting of water-soluble salts and water-soluble saccharides at a concentration exhibiting 1.5–6.0 fold of osmotic pressure of isotonic sodium chloride solution, and (3) at least 0.01 W/W % of an absorption promoter which is at least one N-acyl amino acid derivative or N-acyl peptide derivative represented by the formula:

wherein R is an aliphatic hydrocarbon group, a substituted aliphatic hydrocarbon group, an aromatic hydrocarbon group, a substituted aromatic hydrocarbon group, an aryl-substituted lower hydrocarbon group or a substituted aryl-substituted lower hydrocarbon group; wherein said substituted aliphatic hydrocarbon group, said substituted aromatic hydrocarbon group or said substituted aryl-substituted lower hydrocarbon group is substituted with a member selected from the group consisting of a lower alkyl group, a hydroxyl group, a carboxylic acid group, an alkoxy group, a phosphoric acid group, an amino group, an imino group and a halogen; and A is an amino acid residue or a peptide residue.

2. A suppository according to claim 1, wherein said water-soluble substance is 1 W.W % or more of a water-soluble salt of an alkali metal.

3. A suppository according to claim 2, wherein said water-soluble salt of an alkali metal is a halide, a sulfate, a phosphate or a carbonate of sodium, potassium or lithium.

4. A suppository according to claim 1, wherein said water-soluble substance is 0.25M or more of a water-soluble saccharide.

5. A suppository according to claim 4, wherein said water-soluble saccharide is sorbitol, glucose, mannitol, lactose or sucrose.

6. A suppository according to claim 1, wherein said water-soluble medicine has a partition coefficeint of 50 or less in chloroform/water.

7. A suppository according to claim 1, further comprising an oily vehicle or a water-soluble vehicle.

8. A suppository according to claim 1, wherein R is a member selected from the group consisting of acetic acid, propionic acid, butyric acid, valeric acid, isovaleric acid, hexanoic acid, enathic acid, octanoic acid, pelargonic acid, decanoic acid, undecylic acid, lauric acid, myristic acid, palmitic acid, stearic acid, acrylic acid, crotonic acid, vinylacetic acid, 4-pentenoic acid, oleic acid, linoleic acid, linolenic acid, sorbic acid, benzoic acid, alkylbenzoic acid, phthalic acid, isophthalic acid, o-aminobenzoic acid, a m-aminobenzoic acid, p-aminobenzoic acid, o-hydroxybenzoic acid, m-hydroxybenzoic acid, p-hydroxybenzoic acid, o-alkoxybenzoic acid, m-alkoxybenzoic acid, p-alkoxybenzoic acid, dihydroxybenzoic acid, phenylacetic acid, phenylpropionic acid, o-hydroxy phenylacetic acid, m-hydroxy phenylacetic acid, p-hydroxy phenylacetic acid, phenylmalonic acid, phenylsuccinic acid, cinnamic acid, phenylpyruvic acid and benzoylacetic acid or is an acid substituted with a member selected from the group consisting of a lower alkyl group, a hydroxyl group, a carboxylic acid group, an alkoxy group, a phosphoric acid group, an amino group, an imino group and a halogen, said acid being selected from the group consisting of acetic acid, propionic acid, butyric acid, valeric acid, isovaleric acid, hexanoic acid, enathic acid, octanoic acid, pelargonic acid, decanoic acid, undecylic acid, lauric acid, myristic acid, palmitic acid, stearic acid, acrylic acid, crotonic acid, vinylacetic acid, 4-pentenoic acid, oleic acid, linoleic acid, linolenic acid, sorbic acid, benzoic acid, alkylbenzoic acid, phthalic acid, isophthalic acid, o-aminobenzoic acid, m-aminobenzoic acid, p-aminobenzoic acid, o-hydroxybenzoic acid, m-hydroxybenzoic acid, p-hydroxybenzoic acid, o-alkoxybenzoic acid, m-alkoxybenzoic acid, p-alkoxybenzoic acid, dihydroxybenzoic acid, phenylacetic acid, phenylpropionic acid, o-hydroxy phenylacetic acid, m-hydroxy pehnylacetic acid, p-hydroxy phenylacetic acid, phenylmalonic acid, phenylsuccinic acid, cinnamic acid, phenylpyruvic acid and benzoylacetic acid.

9. A suppository according to claim 1, wherein said N-acyl amino acid derivative or N-acyl peptide derivative is incorporated in said suppository in the form of an alkali metal salt or an ammonium salt.

* * * * *